US012758758B2

(12) United States Patent
Lazoglu et al.

(10) Patent No.: US 12,758,758 B2
(45) Date of Patent: Oct. 13, 2026

(54) IMPLANTABLE CENTRIFUGAL CARDIAC ASSIST PUMP HAVING PERMANENT MAGNETS EMBEDDED IN IMPELLER

(71) Applicant: KOC UNIVERSITESI, Sariyer/Istanbul (TR)

(72) Inventors: Ismail Lazoglu, Sariyer/Istanbul (TR); Caglar Ozturk, Sariyer/Istanbul (TR); Ibrahim Basar Aka, Kadikoy/Istanbul (TR); Deniz Suha Kucukaksu, Uskudar/Istanbul (TR); Vedat Bakuy, Uskudar/Istanbul (TR)

(73) Assignee: KOC UNIVERSITESI, Istanbul (TR)

( * ) Notice: Subject to any disclaimer, the term of this patent is extended or adjusted under 35 U.S.C. 154(b) by 330 days.

(21) Appl. No.: 18/248,659

(22) PCT Filed: Oct. 12, 2020

(86) PCT No.: PCT/TR2020/050940

§ 371 (c)(1),
(2) Date: Apr. 11, 2023

(87) PCT Pub. No.: WO2022/081101

PCT Pub. Date: Apr. 21, 2022

(65) Prior Publication Data

US 2023/0381489 A1 Nov. 30, 2023

(51) Int. Cl.

*A61M 60/232* (2021.01)
*A61M 60/178* (2021.01)
*A61M 60/806* (2021.01)

(52) U.S. Cl.

CPC ........ *A61M 60/232* (2021.01); *A61M 60/178* (2021.01); *A61M 60/806* (2021.01)

(58) Field of Classification Search

CPC .............. A61M 60/232; A61M 60/178; A61M 60/806; A61M 60/419; A61M 60/812; A61M 60/825

See application file for complete search history.

(56) References Cited

U.S. PATENT DOCUMENTS 4,643,641 A 2/1987 Clausen et al.
5,017,103 A 5/1991 Dahl
(Continued)

FOREIGN PATENT DOCUMENTS

WO WO 02/27225 A1 4/2002

OTHER PUBLICATIONS

International Search Report and Written Opinion, dated Jun. 2, 2021, pp. 1-8, issued in International Application No. PCT/TR2020/050940, European Patent Office, Rijswijk, The Netherlands.
(Continued)

*Primary Examiner* — Tammie K Marlen
(74) *Attorney, Agent, or Firm* — Crowell & Moring LLP

(57) ABSTRACT

The present invention relates to a centrifugal flow pump that is suitable for pumping blood that can be used as a left ventricular assist device (LVAD). The present invention more specifically relates to a centrifugal blood pump (100) for effectuating conveying of blood in between an axial inlet (22) and a tangential outlet (23), said centrifugal blood pump (100) comprising a pumping chamber housing an impeller (3) attached onto a rotating hub (11) centered on an axis of rotation and a magnetic drive means magnetically coupled to said impeller (3) for rotating impeller (3), and said impeller (3) comprising blades (9, 10) having a geometry that is configured to minimize hemolysis and thrombosis in said centrifugal blood pump (100).

13 Claims, 6 Drawing Sheets

(56) References Cited

U.S. PATENT DOCUMENTS

| | | | | |
|---|---|---|---|---|
| 5,399,074 | A | 3/1995 | Nośe et al. | |
| 5,458,459 | A | 10/1995 | Hubbard et al. | |
| 5,685,696 | A * | 11/1997 | Zangeneh | F04D 29/284 416/186 R |
| 5,863,179 | A | 1/1999 | Westphal et al. | |
| 2015/0361987 | A1 | 12/2015 | Lin et al. | |
| 2017/0087288 | A1 * | 3/2017 | Groß-Hardt | A61M 60/416 |
| 2018/0010608 | A1 | 1/2018 | Larose et al. | |
| 2019/0015569 | A1 | 1/2019 | Aber et al. | |
| 2020/0407940 | A1 * | 12/2020 | Stewart | E02F 3/92 |

OTHER PUBLICATIONS

Ozturk, Caglar, et al., "Effect of blade curvature on the hemolytic and hydraulic characteristics of a centrifugal blood pump," The International Journal of Artificial Organs, vol. 41, No. 11, pp. 730-737, 2018.

Lazoglu, Ismail, et al., A Short-Term In Vivo Evaluation of the Istanbul Heart Left Ventricular Assist Device in a Pig Model, Experimental and Clinical Transplantation: Official Journal of the Middle East Society for Organ Transplantation, 2019.

* cited by examiner

IMPLANTABLE CENTRIFUGAL CARDIAC ASSIST PUMP HAVING PERMANENT MAGNETS EMBEDDED IN IMPELLER

CROSS-REFERENCE TO RELATED APPLICATIONS

This application is a U.S. National Phase entry under 35 U.S.C. § 371 of International Application No. PCT/TR2020/050940, filed Oct. 12, 2020.

TECHNICAL FIELD OF THE PRESENT INVENTION

The present invention relates to a centrifugal flow pump specially designed to supply blood to the body as a substitute or ventricular assist device of a heart. Said centrifugal flow pump comprises wrapped impeller blades in order to reduce the risk of hemolysis (blood damage).

BACKGROUND OF THE PRESENT INVENTION

Heart diseases are among the most common diseases and the number one cause of death globally. The type of treatment for these diseases depends on their extent and severity. While some patients can be cured with rest and pharmaceutical therapy, there are those severe cases where the only option is heart surgery, including heart transplantation. Due to the shortage in the donor supplies, only about 5,000 heart transplantations can be performed each year in the world. Therefore, mechanical circulatory support systems have become prominent as the only solution for patients with end-stage heart failure and are used as bridge to transplant and even destination therapy.

A ventricular assist device (VAD) is one such mechanical circulatory support system. A VAD is a mechanical pump specially designed to supply blood to the body of a patient with end-stage heart failure. Left Ventricular Assist Devices (LVADs) are the commonly used device for heart failure patients to support blood circulation and assist left ventricle function. In general, these devices increase the quality of life and offer the patients the potential for long-term survival. LVADs consist of two types in terms of mode of operation: pulsatile and rotary (continuous). Currently rotary blood pumps are becoming more common because they are smaller in size, less costly to manufacture, less prone to mechanical damage and they require easier upkeep, therefore having increased durability and longer operational life resulting in improved quality of life for the patients.

Rotary pumps used in LVADs are further divided into two types: axial flow and centrifugal flow. Both flow types utilize a rotary impeller which is the key part of an LVAD. Impeller imparts kinetic energy to the fluid. Also, a diffuser or a volute is implemented to convert this kinetic energy (velocity) to potential energy (pressure). Centrifugal flow blood pumps conventionally comprise a housing defining a pumping chamber and having an axial blood inlet and a tangential volute defining a blood outlet. Said housing may optionally contain a flow straightener in order to minimize pre-rotation of fluid entering the impeller and improve pump efficiency. A rotatable impeller as rotor is housed inside the pumping chamber and is adapted to pressurize blood entering the pumping chamber for exiting at the blood outlet. Said impeller contains one or more magnetic regions, generally in the form of permanent anisotropic magnets embedded in the body thereof. The housing also hosts the motor stator which is magnetically coupled to the impeller, and the impeller is rotated by the magnetic co-relation between the two.

Centrifugal flow blood pumps have superior blood handling properties of centrifugal blood pumps have led them being widely used as cardiac assist devices; however, there are also some disadvantages. The problems associated with current centrifugal flow devices include the following: The small clearances between the rotor and housing and high rotational speeds generate high shear stresses in the blood, causing hemolysis, which is the damage or destruction of the Red Blood Cells (RBC). In addition, possible dead water/wake areas due to flow stagnation can lead to thrombosis (blood clotting), which can affect the pumping mechanism of cardiac assist devices and lead to failure of the device. Furthermore, if the clot circulates in the bloodstream, it might damage the blood vessels in vital organs. Many factors such as the flow rate, pump speed and washout mechanism could contribute to thrombus formation. Furthermore, the hydraulic output, efficiency and the radial force acting on the impeller are critical design parameters, which are difficult to optimize in order to minimize blood damage. Finally, vortex structures are common due to the unstable flow field between the impeller blades and/or shroud region inside the pump. Unstable flow transition and vortex structures reduce hydrodynamic efficiency and increase blood damage potential.

The attempts made in the state of the art to alleviate the problems associated with centrifugal blood pumps as ventricle assist devices are described in the following patents.

US 2018/0010608 discloses a rotary blood pump including a casing defining a pumping chamber, having a blood inlet and a tangential blood outlet. One or more motor stators are provided outside of the pumping chamber. A rotatable impeller having one or more magnetic regions is within the pumping chamber and is adapted to move the blood entering the pumping chamber to the blood outlet. The impeller is radially constrained in rotation by magnetic coupling to one or more motor stators and is axially constrained in rotation by one or more hydrodynamic thrust bearing surfaces on the impeller.

US 2015/0361987 discloses an impeller and rotor structure for a magnetically levitated pump defining a smooth primary flow path and secondary flow path, which extends around an annular magnetic rotor. The shroudless impeller blades are purely radial and overhung from a thin peripheral ring attached to the annular magnetic rotor. A center post having a low aspect ratio extends through the annular rotor. The low aspect ratio is configured to prevent flow in the primary flow path from colliding directly with flow in the secondary flow path at the inner radial gap.

U.S. Pat. No. 5,017,103 discloses a centrifugal blood pump having a pumping chamber provided with an axial inlet and a circumferential outlet and provided with a rotatable impeller having a plurality of radially extending blood propelling vanes. The vanes are configured to each have a blade angle which varies monotonically toward the periphery of the chamber. The impeller is driven by a plurality of magnetizable plates secured to the impeller and a rotatable magnetic drive assembly disposed outside of the impeller housing.

U.S. Pat. No. 5,863,179 discloses a magnetically-driven centrifugal blood pump including a housing and an impeller mounted for rotation within. The impeller includes a generally disk-shaped base plate and a plurality of curvilinear vanes extending axially upward therefrom. The vanes project radially outward from the base plate approximately one-third of their curvilinear length. The curvature of each vane changes along its length, and a tangent angle progresses from the inner end to the outer end according to a preferred formula.

U.S. Pat. No. 5,458,459 discloses a centrifugal pump for pumping biological fluids such as blood including a housing which defines a pumping chamber. The pumping chamber encloses an impeller comprised of a spindle for rotation about a spindle axis and a plurality of blades positioned such that each inner blade end is positioned adjacent to the spindle. The plurality of inner blade ends forms a spin inducer which aids in decreasing hemolysis.

U.S. Pat. No. 5,399,074 discloses a centrifugal blood pump, used for heart-lung machines or the like, comprising an impeller, a casing having a suction inlet and a delivery outlet and being equipped with a space for rotatably accommodating the impeller, and a magnetic drive means disposed outside the casing. The impeller is of a rotationally symmetric shape and has a rotary vane section and a cylindrical section equipped with a magnet means. The vanes of the impeller can have a variety of shapes, such as a curved or straight shape. The magnet drive means for generating a rotating magnetic field coaxially encloses the magnet means of the above-mentioned cylindrical section and rotates the impeller in cooperation with the magnet means.

The present invention aims to improve on the problems in the prior art. The present invention comprises an impeller with blades having a certain wrap angle, blade angles at the hub and shroud, blade lean angle and blade thickness. The impeller is designed for straightening the flow field, reducing the vorticity and improving the hydrodynamic efficiency inside the pump. The proposed impelled blade geometric structure creates a coherent streamline structure with the blades thus reduces the shear stress acting on the red blood cells which leads to a reduced hemolysis level. In addition, the volute profile of the proposed device provides an appropriate velocity field for the given impeller geometry. Furthermore, the volute tongue position at a given tongue angle presents low hemolysis risk by reducing the shear stress field between the impeller and the volute region for the specified pump geometry.

OBJECTS OF THE PRESENT INVENTION

The object of the present invention is to provide a centrifugal flow pump for the conveying of blood to be used as a ventricular assist device with improved performance and reduced danger of hemolysis and thrombus formation.

SUMMARY OF THE PRESENT INVENTION

Left ventricular assist devices (LVADs) are mechanical pumps designed to aid blood circulation in the body of a patient with congestive heart failure. Depending on the patient they can be used as bridge to recovery, bridge to transplant or destination therapy.

LVAD design requires a comprehensive investigation of pump structure and flow dynamics. Blood pumps are designed to work under physiologic flow rates and pressure conditions. Therefore, the pump must generate sufficient hydraulic output. However, any change in the flow field could damage the blood cells and result in hemolysis due to the shear stress acting on the red blood cells. Geometric features of the impeller like the blade angles at the hub and shroud, blade thickness, wrap angle and blade lean angle are crucial for minimizing the risk of hemolysis while still providing sufficient hydraulic performance.

The invention relates to a centrifugal flow rotary blood pump that can function as an implanted LVAD by attaching it to the left ventricle and aorta of a patient with end-stage heart failure. The proposed device is a centrifugal blood pump that utilizes an impeller with wrapped blades with a wrap angle, blade angles at the hub and shroud and blade lean angle chosen to minimize the blood damage by reducing the shear stress and straightening the flow field out.

BRIEF DESCRIPTION OF THE FIGURES OF THE PRESENT INVENTION

Accompanying drawings are given solely for the purpose of exemplifying a centrifugal flow blood pump, whose advantages over prior art were outlined above and will be explained in brief hereinafter.

The drawings are not meant to delimit the scope of protection as identified in the claims nor should they be referred to alone in an effort to interpret the scope identified in said claims without recourse to the technical disclosure in the description of the present invention.

REFERENCED PARTS LIST

Figure 1:
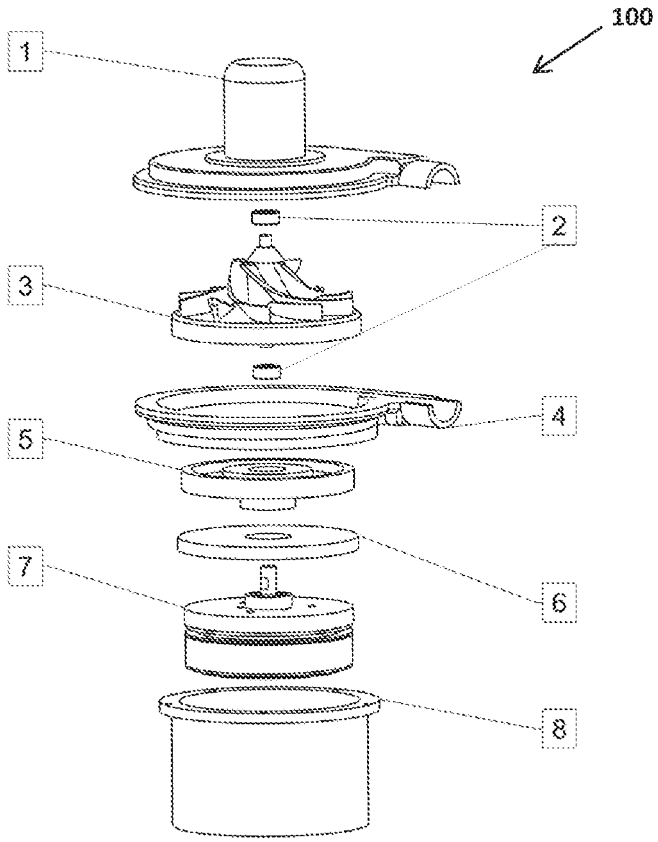
FIG. 1 illustrates an exploded view of a centrifugal blood pump in accordance with the present invention.
Figure 2:
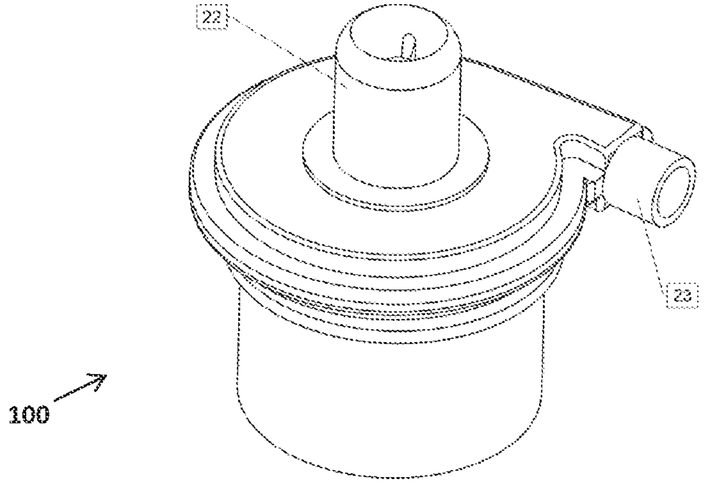
FIG. 2 illustrates an assembled view of a centrifugal blood pump in accordance with the present invention.
Figure 3:
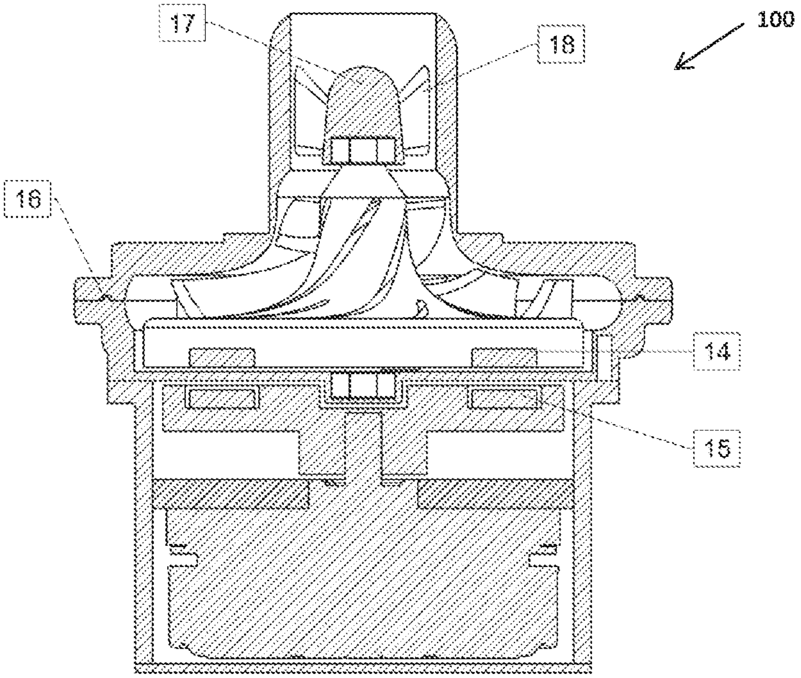
FIG. 3 illustrates a cross-sectional view of a centrifugal blood pump in accordance with the present invention.
Figure 4:
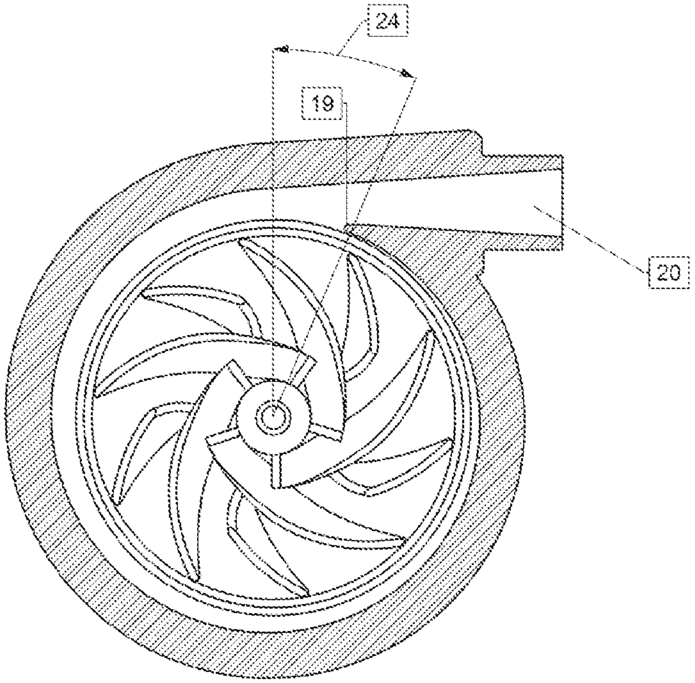
FIG. 4 illustrates a top view of an impeller and bottom housing shroud of a centrifugal blood pump in accordance with the present invention.

1 Top housing shroud
2 Axial sliding bearings
3 Impeller
4 Bottom housing shroud
5 Magnetic rotor disk
6 Motor holder
7 Motor
8 Motor casing
9 Main blades
10 Splitter blades
11 Rotating hub
12 Blade angle at hub

13 Blade angle at shroud
14 Embedded passive magnets
15 Permanent magnets
16 Sealing groove
17 Flow straightener
18 Straight inducer blades
19 Volute tongue
20 Outlet passage
21 Wrap angle
22 Inlet cannula
23 Outlet cannula
24 Tongue angular position
25 Lean angle
100 Centrifugal flow blood pump

DETAILED DESCRIPTION OF THE PRESENT INVENTION

Hemolysis and thrombosis are the major complications associated with mechanical circulatory support devices. These complications are primarily attributed to the high shear stress and flow stagnation inside the blood pump. The impeller is one of the most important regions in blood pumps as it defines the flow field. The blade design parameters including the wrap angle are important since these parameters determine the local absolute velocity which has a great influence on the shearing force. Red blood cells experience high shear force as they pass through narrow openings or high-velocity regions such as blade tips. Ideally, the red blood cells should travel through less unobstructed regions, because the collision between cells and with various parts of the device may contribute to hemolysis with complicated flow patterns. Moreover, the low-velocity regions and recirculation between blade passages are the main contributors to the pump thrombosis. The blood flow between the impeller blades has a high risk of stagnation and thrombosis.

The working principle of centrifugal flow blood pump (100) according to the present invention is similar to other existing mechanical circulatory support devices, in that said centrifugal flow blood pump (100) includes a pumping chamber provided with an axial inlet and a circumferential outlet in addition to a rotatable impeller. The inflow fluid flows through the inlet and then centrifugal kinetic energy is transferred to the fluid by the rotating impeller. The fluid is pushed to the gap between blades and then to the spiral volute where this kinetic energy is converted to the potential energy. These features are described in detail below, in relation to the drawings provided.

In describing the embodiments of the present invention illustrated in the drawings, specific terminology is employed for sake of clarity. However, the present disclosure is not intended to be limited to the specific terminology so selected, and it is to be understood that each specific element includes all technical equivalents which operate in a similar manner.

FIGS. 1-4 show a preferred embodiment of a centrifugal flow blood pump (100) according to the invention. Centrifugal flow blood pump (100) comprises a housing comprised of a top housing shroud (1) and a bottom housing shroud (4) attached via a sealing groove (16) forming a housing shroud, said housing shroud comprising a substantially circular pumping chamber, housing an impeller (3) borne by axial sliding bearings (2) along the axis of rotation, an axial inlet cannula (22) on top housing shroud (1) and a tangential outlet cannula (23) formed by top housing shroud (1) and bottom housing shroud (4). Said inlet cannula (22) houses a flow straightener (17) having straight inducer blades (18) to introduce to blood flow uniformly onto impeller (3). Centrifugal flow blood pump (100) also comprises an outlet passage (20) and volute tongue (19) having a tongue angular position (24). In a preferred embodiment of the invention, tongue angular position (24) is 20°.

Centrifugal blood pump (100) is operated by a magnetic drive means comprising an embedded motor (7) housed in a motor cover housing (8) attached to bottom housing shroud (4). A magnetic rotor disk (5) having embedded permanent magnets (15) is attached to motor (7). Permanent magnets (15) of magnetic rotor disk (5) are coupled to embedded passive magnets (14) with opposite polarity embedded in rotating hub (11) of impeller (3) and imparts the rotation motion from motor (7) to impeller (3), whereby the actuation of impeller (3) is realized.

Figure 5:
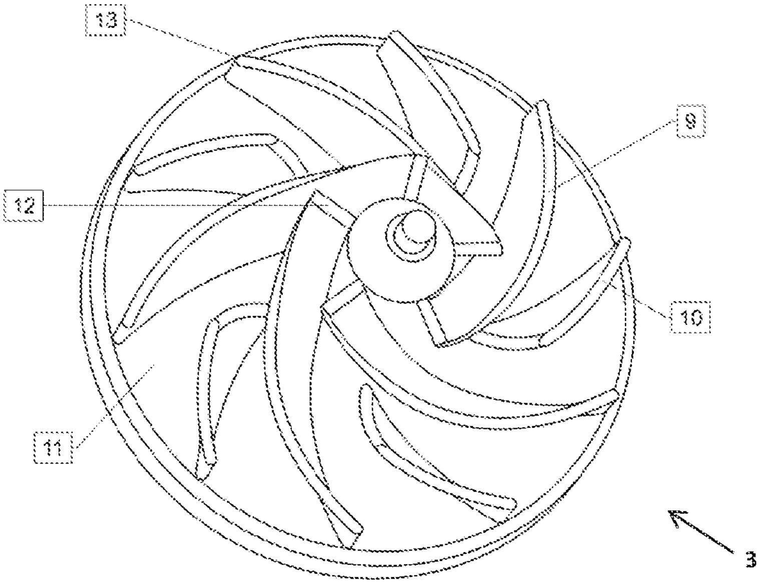
FIG. 5 illustrates a perspective view of an impeller of a centrifugal blood pump in accordance with the present invention demonstrating the blade angles and the hub and shroud.
Figure 6:
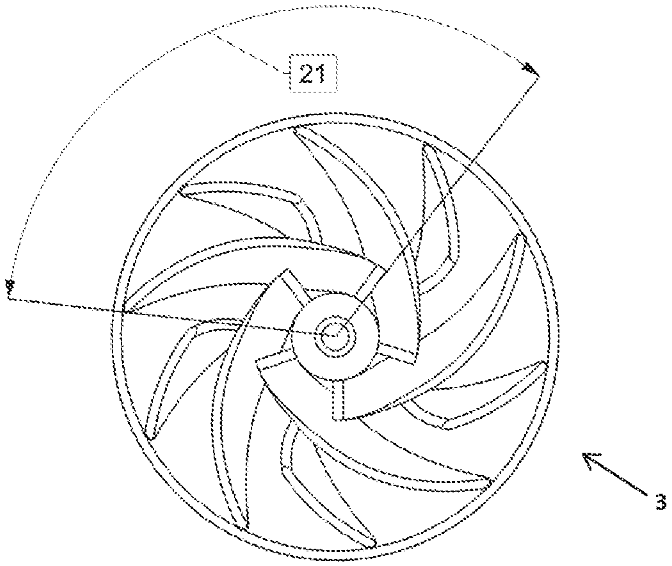
FIG. 6 illustrates a top view of an impeller of a centrifugal blood pump in accordance with the present invention demonstrating the wrap angle.
Figure 7:
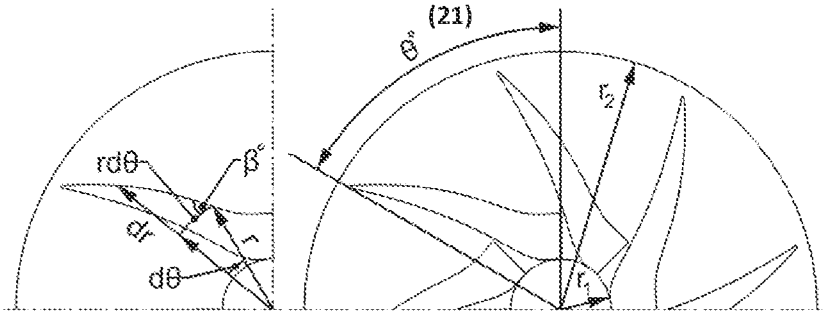
FIG. 7 illustrates the blade definition an impeller of a centrifugal blood pump in accordance with the present invention.

FIGS. 5-7 show a preferred embodiment of an impeller (3) according to the invention. Impeller (3) comprises a rotating hub (11) centered on an axis of rotation with embedded passive magnets (14) and borne by axial sliding bearings (2). Impeller (3) comprises a plurality of main blades (9) and optionally a plurality of splitter blades (10) positioned thereonto.

The number of the blades of impeller plays an important role in terms of high speed centrifugal pump head, efficiency and cavitation. In a preferred embodiment of the invention impeller (3) comprises five main blades (9) and five splitter blades (10).

It was mentioned above that the geometrical parameters of pump components play an important role in the performance characteristics, and the unique combination of geometrical parameters rather than the working principle usually creates the novelty for LVADs. A well-matching impeller and volute structure facilitates a blood pump with low hemolysis and thrombosis. Centrifugal blood pump (100) comprises an impeller (3) with a geometry that has a specific wrap angle (21) range coupled with a specific number of blades and lean angle distribution. The disclosed impeller (3) geometry provides a well-guided blood flow between the impeller blades and reduces the stagnation zones and high shear stress in the flow field. Experimental hemolysis results in flow loop tests also confirm that the disclosed blood pump geometry provides low hemolysis with 1 mg/100 L NIH (Normalized Index of Hemolysis) value.

The blade curvature has a significant impact on both hydraulic and hemolytic performances of the pump. Flow separation and vortex formation around the blade trailing edges can be observed for straight-blade impellers, which are both major concerns for hemolysis generation. Introducing a blade curvature creates a narrower flow path and thus provides enhanced guidance to the fluid. However, an excessive blade curvature increases the blade length, reduces the priming volume, and obstructs the flow passage due to the narrower flow path (C. Ozturk, I. B. Aka, and I. Lazoglu, "Effect of blade curvature on the hemolytic and hydraulic characteristics of a centrifugal blood pump," The International journal of artificial organs, vol. 41, no. 11, pp. 730-737, 2018). The effect of the wrap angle (21) over hemolysis was investigated by utilizing a computational prediction model. Three different hemolysis estimation models were employed as the stress-based, strain-based and Lagrangian models which are widely used in the literature. The blood damage index (D) of three different hemolysis models were estimated by in-silico analysis and given in Table 1 below.

TABLE 1

Blood Damage Comparison of Blade Wrap Angle

| Wrap Angle | 0° | 60° | 120° |
|---|---|---|---|
| Blood Damage Index by Stress-based Model | $1.40 \times 10^{-3}$ | $1.30 \times 10^{-3}$ | $1.28 \times 10^{-3}$ |
| Blood Damage Index by Strain-based Model | $3.27 \times 10^{-4}$ | $3.19 \times 10^{-4}$ | $2.72 \times 10^{-4}$ |
| Blood Damage Index by Lagrangian Model | $3.26 \times 10^{-2}$ | $2.90 \times 10^{-2}$ | $1.38 \times 10^{-2}$ |

It can be observed in Table 1 that blood damage indices are decreasing as the wrap angle (21) changes from 0° to 120°. Due to a better-guided flow induced by a larger wrap angle (21), the blood pump with a wrapped blade impeller produces lower blood damage indices. All hemolysis estimation methods confirm that a high wrap angle (21) provides lower hemolysis value. This may be a result of better guidance of the streamline in the impeller region and consequently lower generation of vortical structures. Based on the extensive in-silico analysis of various blade wrap angles (21), the optimal hydraulic and hemolytic performance were achieved for the blood pumps which comprise main blades (9) and splitter blades (10) configured to have a blade wrap angle (21) in the range of 100°-125°. In a preferred embodiment of the invention, blade wrap angle (21) is in the range of 120°-125°.

Figure 8:
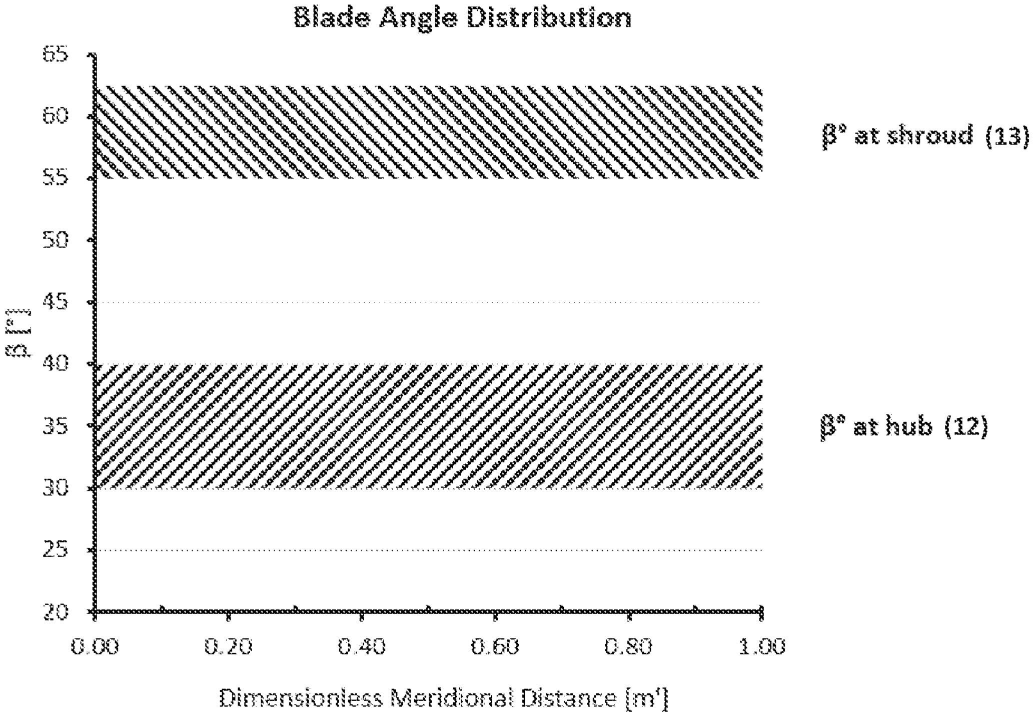
FIG. 8 illustrates the blade angle range at hub and shroud of an impeller of a centrifugal blood pump in accordance with the present invention.

In addition, main blades (9) and splitter blades (10) are configured to each have a blade angle (β) which varies along the impeller (3) from the shroud to the hub. The blade angle (β) distribution of a preferred embodiment of the invention is shown in FIG. 8. Blade angle at hub (12) is defined as the blade angle (β) formed by a line drawn tangent to leading edge of blades (9, 10) on the impeller entrance (hub) side and the tangent line at the impeller entrance (hub) end of each blade (9, 10). In a preferred embodiment of the invention, blade angle at hub (12) is in the range of 30°-40° at the hub (11). Blade angle at shroud (13) is defined as the blade angle (β) formed by the tangent line at the impeller discharge (shroud) trailing edge of each blade (9, 10) and line drawn tangent to impeller's (3) lower end section at the impeller discharge (shroud) trailing edge of each blade (9, 10). In a preferred embodiment of the invention, blade angle at shroud (13) is in the range of 55°-62.5° at the shroud.

Figure 9:
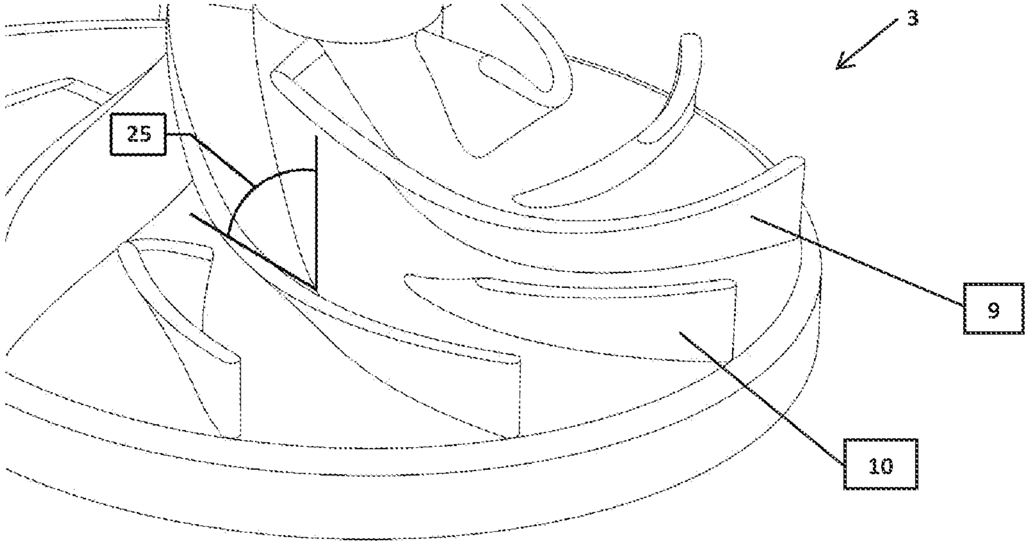
FIG. 9 illustrates the blade lean angle definition of a centrifugal blood pump in accordance with the present invention.
Figure 10:
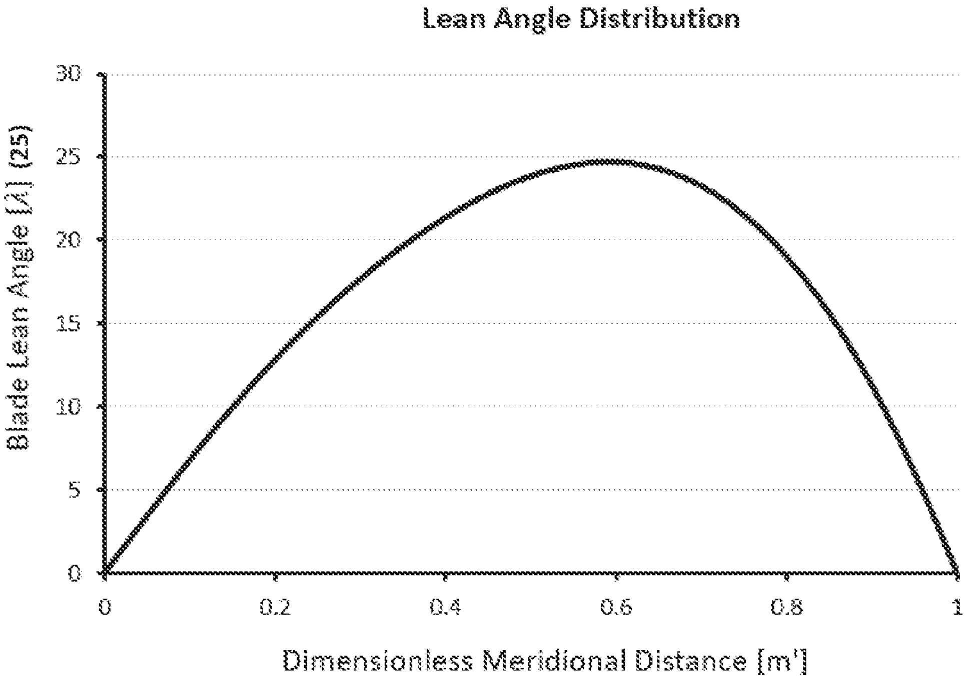
FIG. 10 illustrates the blade lean angle distribution along the meridional distance of an impeller of a centrifugal blood pump in accordance with the present invention.

FIG. 9 shows the definition of blade lean angle (λ) (25) as the slope between blade mean lines in circumferential direction and FIG. 10 shows the distribution of blade lean angle (λ) (25) as a function of dimensionless meridional distance (m'). This dynamic lean angle (25) provides a change in the blade angle from the impeller hub to the impeller shroud, with the blade angle increasing towards the impeller shroud. The blade lean angle (25) is defined as a polynomial degree of the third degree as given below, wherein m' is the dimensionless meridional distance and a, b, c, and d are constants.

$$\text{Blade Lean Angle } (\lambda) = a\,m'^3 + b\,m'^2 + cm' + d$$

In a preferred embodiment of the invention, a=−66.4; b=4.3; c=61.8 and d=0.1, and blade lean angle (λ) (25) is in the range of 0°-25°.

In a preferred embodiment of the invention, the radial distance of the impeller blades can be adjusted in the range 9-18 mm, the impeller entrance (hub) has a radius in the range r1=3-6 mm and the impeller discharge (shroud) has a radius in the range r2=12-24 mm.

In a preferred embodiment of the invention, said splitter blades (10) have an angular offset of 50% (0.5 angular offset/pitch fraction) corresponding to the main blade (9). The location of splitter blades (10) is expressed as the fraction of the blade's meridional length. The leading edge of splitter blades (10) corresponds to a cut-off value at hub and shroud. In a preferred embodiment of the invention, the fraction is 0.45 at the hub and 0.6 at the shroud.

In a preferred embodiment of the invention, each blade (9, 10) has a thickness of 1 mm and blades (9, 10) are rounded with the elliptic ratio of 2.0 at the leading edge and trailing edge.

Figure 11:
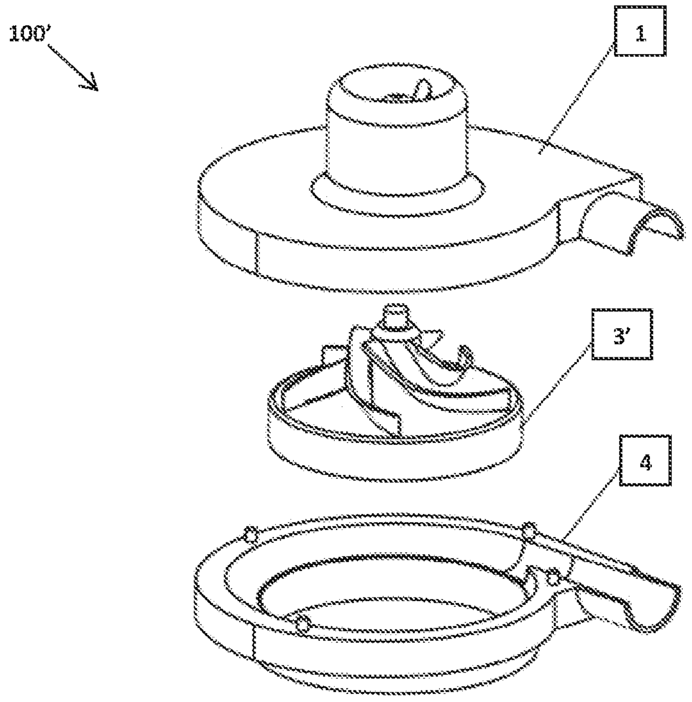
FIG. 11 illustrates an exploded view of an alternative embodiment of a centrifugal blood pump in accordance with the present invention.

FIG. 11 shows an alternative embodiment of centrifugal blood pump (100') comprising an impeller (3') having five main blades (9) attached onto a rotating hub (11), centered on an axis of rotation with embedded passive magnets.

The present invention provides a well-matching impeller and volute structure that facilitates a blood pump with low hemolysis and thrombosis. The disclosed impeller geometry provides well-guided blood flow between the impeller blades and reduces the stagnation zones and high shear stress in the flow field. The disclosed blood pump geometry comprising an impeller with blades having a certain wrap angle, blade angles at the hub and shroud, blade lean angle (25) and blade thickness results in lower hemolysis, as tested in-silico, in-vitro, and acute in-vivo tests (C. Ozturk, I. B. Aka, and I. Lazoglu, "Effect of blade curvature on the hemolytic and hydraulic characteristics of a centrifugal blood pump," The International journal of artificial organs, vol. 41, no. 11, pp. 730-737, 2018; I. Lazoglu et al., "A Short-Term In Vivo Evaluation of the Istanbul Heart Left Ventricular Assist Device in a Pig Model," Experimental and clinical transplantation: official journal of the Middle East Society for Organ Transplantation, 2019).

In a nutshell, the present invention proposes a centrifugal blood pump (100) for effectuating conveying of blood in between an axial inlet cannula (22) and a tangential outlet cannula (23), said centrifugal blood pump (100) comprising a housing shroud comprising a pumping chamber housing an impeller (3) comprising embedded passive magnets (14) and a rotating hub (11) centered on an axis of rotation, and a magnetic drive means magnetically coupled to said impeller (3) for actuating the rotation of impeller (3), and said impeller (3) comprising a plurality of main blades (9) attached onto said rotating hub (11).

In one variation of the present invention, said main blades (9) are configured to have blade wrap angle (21) in the range of 100°-125°.

In a further variation of the present invention, said main blades (9) are configured to have blade angle at hub (12) in the range of 30°-40°.

In a further variation of the present invention, said main blades (9) are configured to have blade angle at shroud (13) in the range of 55°-62.5°.

In a further variation of the present invention, said main blades (9) are configured to have blade lean angle (λ) (25) in the range of 0°-25°.

In a further variation of the present invention, said main blades (9) are configured to have blade wrap angle (21) in the range of 120°-125°.

In a further variation of the present invention, each blade (9) is configured to have variable blade lean angle (λ) (25) calculated using the formula $$\text{Blade Lean Angle } (\lambda)=a\,[\![m']\!]\hat{}3+b\,[\![m']\!]\hat{}2+cm'+d$$

wherein m' is the dimensionless meridional distance and a=−66.4; b=4.3; c=61.8 and d=0.1.

In a further variation of the present invention, said impeller (3) comprises a plurality of splitter blades (10).

In a further variation of the present invention, said splitter blades (10) have an angular offset of 50% corresponding to the main blade (9).

In a further variation of the present invention, said impeller (3) comprises five main blades (9).

In a further variation of the present invention, said impeller (3) comprises five splitter blades (10).

In a further variation of the present invention, each blade (9) is rounded with the elliptic ratio of 2.0 at the leading edge and trailing edge.

In a further variation of the present invention, said magnetic drive means comprises an embedded motor (7), a magnetic rotor disk (5) having embedded permanent magnets (15) attached to motor (7) housed in a motor cover housing (8) attached to said housing shroud, and permanent magnets (15) of magnetic rotor disk (5) are coupled to embedded passive magnets (14) with opposite polarity embedded impeller (3) for actuating the rotation of impeller (3).

In a further variation of the present invention, said impeller (3) is borne by axial sliding bearings (2) along the axis of rotation.

In a further variation of the present invention, said inlet cannula (22) houses a flow straightener (17) having straight inducer blades (18).

The invention claimed is:

1. A centrifugal blood pump for effectuating conveying of blood in between an axial inlet cannula and a tangential outlet cannula, said centrifugal blood pump comprising:
- a housing shroud comprising a pumping chamber housing an impeller comprising embedded passive magnets and a rotating hub centered on an axis of rotation, and a magnetic drive means magnetically coupled to said impeller for actuating the rotation of impeller, and said impeller comprising a plurality of main blades attached onto said rotating hub characterized in that;
- said main blades have a blade wrap angle in the range of 100°-125°,
- said main blades have a blade angle at hub in the range of 30°-40°,
- said main blades have a blade angle at shroud in the range of 55°-62.5°, and
- said main blades have a continuously variable blade lean angle (λ) in the range of 0°-25°, wherein the blade lean angle is at a maximum at a central portion of the main blades along a distance between the rotating hub and the shroud, and the blade lean angle is at a minimum at the rotating hub and the shroud.

2. A centrifugal blood pump as set forth in claim 1, wherein the blade wrap angle is in the range of 120°-125°.

3. A centrifugal blood pump as set forth in claim 1, wherein; each blade has a variable blade lean angle (λ) calculated using the formula $$\text{Blade Lean Angle } (\lambda)=am'^3+bm'^2+cm'+d$$

wherein m' is a dimensionless meridional distance and a=−66.4; b=4.3; c=61.8 and d=0.1.

4. A centrifugal blood pump as set forth in claim 1, wherein; said impeller comprises a plurality of splitter blades.

5. A centrifugal blood pump as set forth in claim 4, wherein; said splitter blades have an angular offset of 50% corresponding to the main blades.

6. A centrifugal blood pump as set forth in claim 1, wherein; said impeller comprises five main blades.

7. A centrifugal blood pump as set forth in claim 6, wherein; said impeller comprises five splitter blades.

8. A centrifugal blood pump as set forth in claim 1, wherein; each blade comprises a leading edge and a trailing edge, which are rounded with an elliptic ratio of 2.0 at each of the leading edge and the trailing edge.

9. A centrifugal blood pump as set forth in claim 1, wherein; said magnetic drive means comprises an embedded motor, a magnetic rotor disk having embedded permanent magnets attached to motor housed in a motor cover housing attached to said housing shroud, and permanent magnets of magnetic rotor disk are coupled to embedded passive magnets with opposite polarity embedded in the impeller for actuating the rotation of impeller.

10. A centrifugal blood pump as set forth in claim 1, wherein; said impeller is disposed between axial sliding bearings along an axis of rotation.

11. A centrifugal blood pump as set forth in claim 1, wherein; said inlet cannula houses a flow straightener having straight inducer blades.

12. The centrifugal blood pump as set forth in claim 1, wherein the maximum of the blade lean angle is at about a dimensionless meridional distance of about 0.6 along the main blades from the hub to the shroud.

13. The centrifugal blood pump as set forth in claim 1, wherein the maximum of the blade lean angle is about 25° at the central portion of the main blades and the minimum blade lean angle is about 0° at the hub and the shroud.

* * * * *